US008221767B2

(12) United States Patent
Dhar et al.

(10) Patent No.: US 8,221,767 B2
(45) Date of Patent: Jul. 17, 2012

(54) ANTIGENICITY OF INFECTIOUS PANCREATIC NECROSIS VIRUS VP2 SUB-VIRAL PARTICLES EXPRESSED IN YEAST

(75) Inventors: Arun K. Dhar, Sykesville, MD (US); Robert M. Bowers, Boulder, CO (US); F. C. Thomas Allnutt, Glenwood, MD (US)

(73) Assignee: Advanced Bionutrition Corporation, Columbia, MD (US)

( * ) Notice: Subject to any disclaimer, the term of this patent is extended or adjusted under 35 U.S.C. 154(b) by 224 days.

(21) Appl. No.: 12/519,991

(22) PCT Filed: Dec. 18, 2007

(86) PCT No.: PCT/US2007/087942
§ 371 (c)(1),
(2), (4) Date: Dec. 10, 2009

(87) PCT Pub. No.: WO2008/140610
PCT Pub. Date: Nov. 20, 2008

(65) Prior Publication Data
US 2010/0092521 A1    Apr. 15, 2010

Related U.S. Application Data

(60) Provisional application No. 60/875,901, filed on Dec. 20, 2006.

(51) Int. Cl.
*A61K 38/00* (2006.01)
*C12P 19/34* (2006.01)
(52) U.S. Cl. .................. 424/204.1; 424/93.1; 424/1.17; 435/91.32
(58) Field of Classification Search .................. None
See application file for complete search history.

(56) References Cited

U.S. PATENT DOCUMENTS

| 6,936,256 | B2 | 8/2005 | Vakharia |
|---|---|---|---|
| 2004/0081638 | A1 | 4/2004 | Kyle |
| 2004/0177392 | A1 | 9/2004 | Barratt et al. |
| 2006/0024404 | A1 | 2/2006 | Kyle |
| 2006/0120999 | A1 | 6/2006 | Dhar et al. |
| 2006/0121468 | A1 | 6/2006 | Allnutt et al. |
| 2006/0127453 | A1 | 6/2006 | Harel |
| 2006/0130162 | A1 | 6/2006 | Kyle et al. |
| 2007/0082008 | A1 | 4/2007 | Harel et al. |
| 2007/0292952 | A1 | 12/2007 | Dhar et al. |
| 2008/0044481 | A1 | 2/2008 | Harel |
| 2008/0194504 | A1 | 8/2008 | Kyle et al. |
| 2009/0181363 | A1 | 7/2009 | Dhar |
| 2009/0238890 | A1 | 9/2009 | Piechocki et al. |
| 2009/0246184 | A1 | 10/2009 | Harel et al. |

FOREIGN PATENT DOCUMENTS

| WO | 02/38770 | 5/2002 |
|---|---|---|
| WO | WO0238770 A1 * | 5/2002 |
| WO | WO 02/076391 | 10/2002 |
| WO | WO 03/089579 | 10/2003 |
| WO | WO 03/103692 | 12/2003 |
| WO | WO 2004/043139 | 5/2004 |
| WO | WO 2006/122299 | 11/2006 |
| WO | WO 2007/067207 | 6/2007 |
| WO | WO 2007/117511 | 10/2007 |
| WO | WO 2008/076975 | 6/2008 |
| WO | WO 2008/140610 | 11/2008 |

OTHER PUBLICATIONS

Labus et al. Fish & Shellfish Immunology, 2001, vol. 11, pp. 203-216.*
Dhar et al. Antiviral Research 2010, vol. 85, pp. 525-531.*
Bottcher, B., N. A. Kiselev, V. Y. Stel'Mashchuk, N. A. Perevozchikova, A. V. Borisov, and R. A. Crowther. 1997. Three-dimensional structure of infectious bursal disease virus determined by electron cryomicroscopy. J Virol 71(1): 325-330.
Christie, K.E. 1997. Immunization with vital antigens: infectious pancreatic necrosis, Dev. Biol. Stand. 90: 191-199.
Duncan, R., Mason, C. L., Nagy, E., Leong, J. A., Dobos, P., 1991. Sequence analysis of infectious pancreatic necrosis virus genome segment B and its encoded VP1 protein: a putative RNA-dependent RNA polymerase lacking the GIy-Asp-Asp motif. Virology 181(2), 541-552.
Melby, H.P., P. Caswell-Reno, and K. Falk. 1994. Antigenic analysis of Norwegian aquatic birnavirus isolates uwin monoclonal antibodies J. Fish Dis. 17: 85-91. McKenna, B. M., R. M. Fitzpatrick, K. V. Phenix, D. Todd, L. M. Vaughan and G. J. Atkins, 2001. Formation of infectious pancreatic necrosis virus-like particles following expression of segment A by recombinant semliki forest virus. Marine Biotechnology 3(2): 103-110.
Magyar, G. and P. Dobos. 1994. Evidence to the detection of the infectious pancreatic necrosis virus polyprotein and the 17 kDa polypeptide in infected cells and the NS protease in purified virus. Virology 204(2): 580-589.
Labus, M. B., S. Breeman, A. E. Ellis, D. A. Smail, M. Kervick and W. T. Melvin. 2001. Antigenic comparison of a truncated form of VP2 of infectious pancreatic necrosis (IPN) virus expressed in four different cell types. Fish & Shellfish Immunology 11(3): 203-216.

(Continued)

*Primary Examiner* — Bao Li
(74) *Attorney, Agent, or Firm* — Marianne Fuierer; Moore & Van Allen, PLLC

(57) ABSTRACT

Infectious pancreatic necrosis virus (IPNV), the etiologic agent of infectious pancreatic necrosis in salmonid fish, causes significant losses to the aquaculture industry. The gene for the viral capsid protein (VP2) was cloned into a yeast expression vector and expressed in *Saccharomyces cerevisae*. Expression of the capsid gene in yeast resulted in formation of approximately 20 nanometer sub-viral particles composed solely of VP2 protein. Anti-IPNV antibodies were detected in rainbow trout vaccinated either by injection of purified VP2-subviral particles (rVP2-SVP) or by feeding recombinant yeast expressing rVP2-SVP. Challenge of rVP2-SVP immunized trout with a heterologous IPNV strain and subsequent viral load determination showed that both injection and orally vaccinated fish had lower IPNV loads than naive or sham-vaccinated fish. This study demonstrates the ability of rVP2-SVPs to induce a specific immune response and the ability of immunized fish to reduce the viral load after an experimentally induced IPNV infection. The invention is not limited to IPNV, and is applicable to other similar viruses for which SVPs can be made and administered to fish.

8 Claims, 5 Drawing Sheets

OTHER PUBLICATIONS

Heppell J., E. Tarrab, J. Lecomte, L. Berthiaume, and M. Arella. 1995. Strain variability and localization of important epitopes on the major structural protein (VP2) of infectious pancreatic necrosis virus. Virology 214 (1): 40-49.

Gorbalenya, A. E., F. M. Pringle, J. L. Zeddam, B. T. Luke, C. E. Cameron, J. Kalmakoff, T. N. Hanzlik, K. H. Gordon, and V. K. Ward, 2002. The palm subdomain-based active site is internally permuted in viral RNA-dependent RNA polymerases of au ancient lineage, J. Mol. Biol. 324 (1): 47-62.

Galloux, M., C. Chevalier, C. Henry, J.-C. Huet, B. Da Costa, B. Delmas. 2004. Peptides resulting from the pVP2 C-terminal processing are present in infectious pancreatic necrosis virus particles. J. Gen. Virol. 85(Pt 8): 2231-2236.

Frost P., L. S. Havarstein, B. Lygren, S. Stahl, C. Endresen, K. E. Christie. 1995. Napping of neutralization epitopes on infectious pancreatic necrosis viruses. J. Gen. Virol. 76 (Pt 5): 1165-1172.

Pitcovski, J., B. Gutter, et al. (2003). "Development and large-scale use of recombinant VP2 vaccine for the prevention of infectious bursal disease of chickens." Vaccine 21(32): 4736-43.

Romanos, M. A., C. A. Scoer, and J. J. Clare, 1992. Foreign gene expression in yeast: a review. Yeast 8(6): 423-488.

Roberts, R. J. and M. D. Pearson 2005. Infectious pancreatic necrosis in Atlantic salmon, Salmo salar L. J. Fish Diseases 28(7): 383-390.

Pous, J., C. Chevalier, M. Ouldali, J. Navaza, B. Delmas and J. Lepault. 2005. Structure of birnavirus-like particles determined by combined electron cryomicroscopy and X-ray crystallography. J. Gen. Virol. 86(Pt 8): 2339-2346.

Pannunzio, V.G., Burgos, H.I., Alonso, M., Ramos, E.H., Mattoon, J.R., Stella, CA. 2004. Yeast Plasmids with the Least Trouble. Promega Notes #87: 27-28.

Dobos, P., 1995. The molecular biology of infectious pancreatic necrosis virus (IPNV). Ann. Rev. Fish Dis. 5, 24-54.

Biering, E., S. Villoing, I. Sommerset, K. E. Christie. 2005. Update on viral vaccines for fish In: P. J. Midtlyng (ed.), Progress in Fish Vaccinology. Dev. Biol. Basel 121 : 97-113.

* cited by examiner

SEQUENCE LISTING

<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Synthetic construct

<400> SEQUENCE: 1
gagatctatg aacacaacaa aggcaaccgc                              30

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
aagcttaagc ccatgtgtcc atgac                                   25

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3

```
<210> SEQ ID NO 4
<211> LENGTH: 27
<212> TYPE: DNA
<213> ORGANISM: Artificial Sequence
<220> FEATURE:
<223> OTHER INFORMATION: Synthetic Construct

<400> SEQUENCE: 4
ataagcttgg gggcccctg gggggcc                                           27

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
aggagatgac atgtgctaca ccg                                              23

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
ccagcgaata ttttctccac ca                                               22

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
tgatctacaa gtgcggaggc a                                                21

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
cagcacccag gcatacttga a                                                21
```

ANTIGENICITY OF INFECTIOUS PANCREATIC NECROSIS VIRUS VP2 SUB-VIRAL PARTICLES EXPRESSED IN YEAST

CROSS-REFERENCE TO RELATED APPLICATIONS

This application is filed under the provisions of 35 U.S.C. §371 and claims the priority of International Patent Application No. PCT/US07/087,942 filed on Dec. 18, 2007, which in turn claims priority of U.S. Provisional Application No. 60/875,901 filed on Dec. 20, 2006, the contents of which are incorporated by reference herein for all purposes.

BACKGROUND OF THE DISCLOSURE

1. Field of Invention

The disclosure relates generally to the fields of immunology and fish production.

2. Related Art

Infectious pancreatic necrosis virus is the causative agent of infectious pancreatic necrosis disease (IPN) that infects salmonids and remains a serious problem in the aquaculture industry (1). IPN is especially contagious and destructive to juvenile trout and salmon. Highly virulent strains may cause greater than 70% mortality in hatchery stocks over a period of two months (21). This disease is especially destructive in salmonid eggs and fingerlings (25). Survivors of infection can remain lifelong asymptomatic carriers and serve as reservoirs of infection, shedding virus in their feces and reproductive products. Losses due to IPNV on salmon smoltification have been estimated at 5% (16). Economic losses due to IPNV in aquaculture were estimated to be over $60 million in 1996 (4), (17). This has been reduced as vaccines for salmonids became available based on killed virus or recombinantly produced viral peptides (13, 17). However, these vaccines are not completely effective and can only be used in fairly large fish due to the reliance on injection for vaccination.

IPNV is a double-stranded RNA virus of the Birnaviridae family (5) and is the type species of the Aquabirnavirus genus (6). Birnaviruses have a non-enveloped, single-shelled particle structure comprised of a single protein capsid layer with T=13 icosahedral symmetry (2). All birnavirus genomes have two dsRNA segments. The IPNV genome's two dsRNA segments are designated segments A and B. Segment B (2777 nucleotides) encodes a minor internal polypeptide VP1 (94 kDa), which is the virion-associated RNA-dependent RNA polymerase (RdRp) (7), (11). Segment A (3097 nucleotides) encodes a 106-kDa precursor polyprotein composed of pVP2-VP4-VP3, in that order, and a 15-kDa non-structural VP5 protein, found only in infected cells (14). VP2 and VP3 are the major capsid proteins, but VP2 is the major host-protective antigen of IPNV (9), (12).

There are commercial multivalent vaccines based on inactivated whole virus available as well as those produced with another approach, expressing VP2-derived conserved antigenic epitopes in bacteria for production of a subunit vaccine. In the laboratory, these current vaccines provide impressive protection against bath challenge with IPNV, but the behavior in the field is not predicted by the laboratory studies. This could be due to the lack of a well-defined challenge system with mortality as its endpoint. Results based on viral clearance exist but may not be as rigorous as a standardized challenge model (1). Another possible explanation could be that the salmon smolts or larger trout being vaccinated are already infected with the virus, as each year between 30-40% of the salmon hatcheries experience an outbreak of IPN (3) and IPN is endemic in many trout rearing areas. The need for better field efficacy could be achieved with improved vaccines that could be economically delivered to young salmonids such that subsequent vaccinations would boost existing immunity instead of trying to combat an existing acute or chronic infection.

BRIEF SUMMARY OF THE SEVERAL VIEWS OF THE DRAWINGS

FIG. 1A illustrates VP2 under the GAL 10 promoter. FIG. 1B illustrates VP2 and VP3 under the GAL 10 and GAL 1 promoters, respectively.

FIG. 2, consisting of FIGS. 2A and 2B, includes images of SDS-PAGE and immunoblot analysis of crude yeast lysates from recombinant yeast clones containing the IPNV VP2 gene or VP2 and VP3 genes.

FIG. 4A is a graph for fish injected with purified rVP2-SVPs by intraperitoneal injection. The treatments for the intraperitoneally vaccinated group include fish vaccinated with rVP2-SVPs (filled bar, n=12), adjuvant only control fish (open bar, n=8), and naive (non-immunized) fish (spotted bar, n=9). FIG. 4A is a graph for fish vaccinated orally with yeast expressing rVP2-SVPs. The treatments for the oral vaccinated group include fish fed diets containing recombinant yeast expressing rVP2-SVPs (checkered bar, n=12), non recombinant yeast (striped bar, n=1 1), and naive (non-immunized) fish (spotted bar, n=9). The error bars represent 1 SEM.

FIG. 5, consisting of FIGS. 5A and 5B, is a pair of bar graphs that illustrate the relative load of IPNV in spleen tissue of vaccinated and non-immunized rainbow trout as determined by SYBR Green real-time RT-PCR.

DETAILED DESCRIPTION

Figure 1:
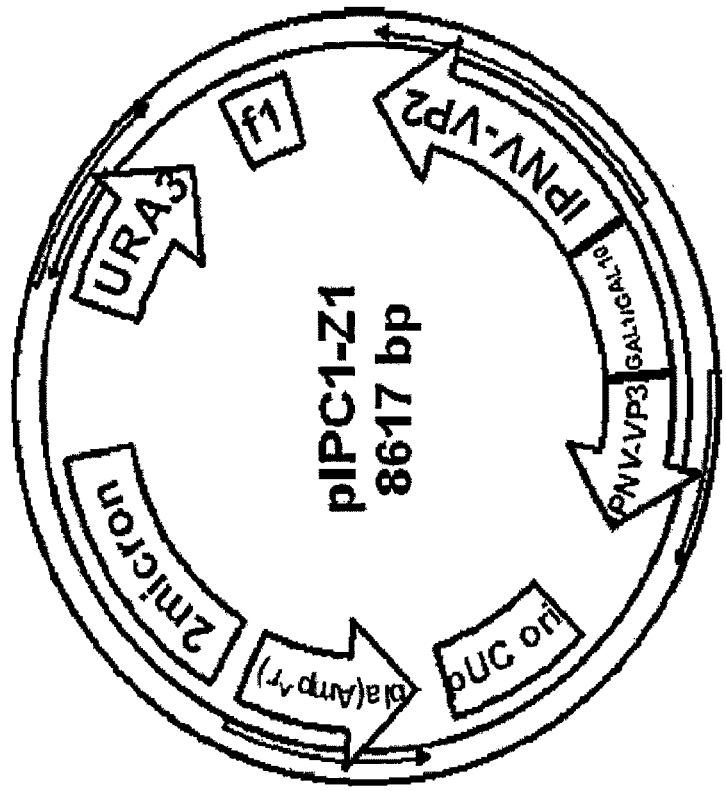
FIG. 1, consisting of FIGS. 1A and 1B, shows pESC-ura expression vector maps containing IPNV genes VP2 and VP3.
Figure 1:
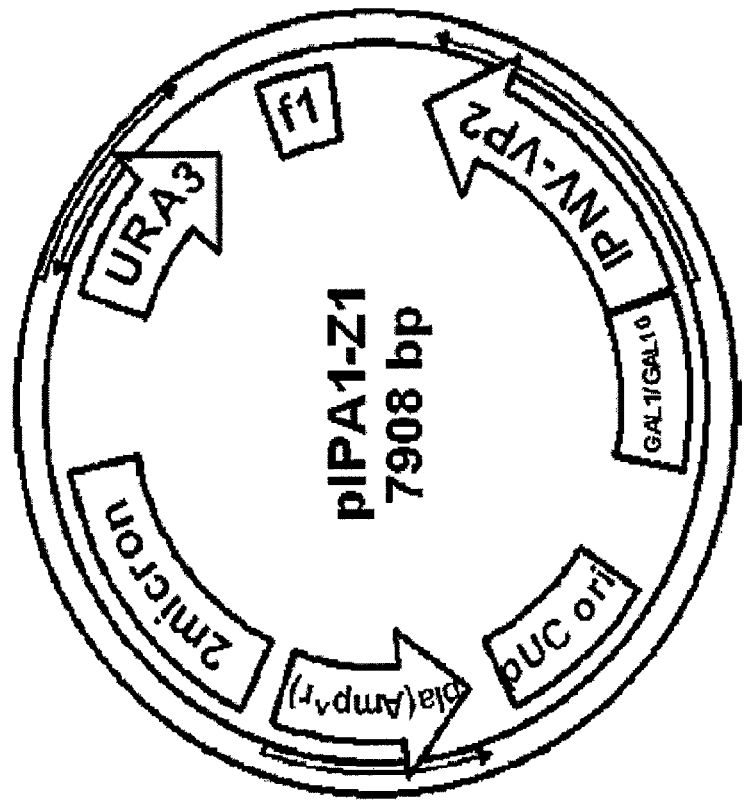

The disclosure relates to production and care of fish, including immunization of fish against viral pathogens.

Here, we report cloning of the IPNV-VP2 gene into a yeast expression vector, pESC-ura. Expression of the VP2 protein resulted in formation of approximately 20 nanometer subviral particles (SVPs) in yeast, as detected by electron microscopy. Purified recombinant VP2 SVPs (rVP2-SVPs) were used to vaccinate fish by both injection and oral routes and their antigenicity in rainbow trout evaluated by immunoassay. An IPNV challenge trial was also carried out and the effect of vaccination on viral load evaluated.

An ideal vaccine for IPNV must induce long lasting protection at an early age, prevent carrier formation, and be effective against a large number IPNV serotypes. Injection cannot be used for small fish, therefore either oral delivery or immersion are more preferred routes for early vaccination. These attributes of an ideal IPNV vaccine must be met either by a recombinant subunit vaccine or by an inactivated viral vaccine, as a live attenuated vaccine could potentially lead to carrier formation. The yeast expression system has potential value for oral vaccine development, since yeast is already a component of feeds and is generally regarded as safe. This contrasts with bacterial expression in *Escherichia coli*, which generates pyrogens that would need to be removed before use of any crude preparation as an oral vaccine (22). The use of yeast is also attractive because production is economical and, through well-developed genetic systems, can be engineered to provide an abundant supply of the protein or proteins of interest. In fact, Pitcovski et al. (19) reported the development and large-scale use of yeast-derived recombinant VP2 vaccine for the prevention of infectious bursal disease (caused by another birnavirus) of chickens.

Materials and Methods

Cloning of the VP2 and VP3 Genes of IPNV

The West Buxton (WB) strain of IPNV, obtained from American Type Culture Collection (ATCC VR-877), was used for this study. This virulent strain of IPNV is prevalent in Maine and Canada, where the major North American salmon aquaculture industry exists. The WB strain of IPNV was purified as previously described (26). The virus was propagated in Chinook salmon embryo (CHSE-214) cell cultures (ATCC CRL-1681), maintained at 15 degrees Celsius in Eagle's minimal essential medium (EMEM) and supplemented with 10% fetal bovine serum (FBS), 100 units per milliliter penicillin, 100 micrograms per milliliter streptomycin and 1 microgram per milliliter fungizone. Total viral RNA was isolated from purified virus by digesting with proteinase K (200 micrograms per milliliter final concentration) followed by phenol: chloroform extraction (23). The IPNV-VP2 and VP3 genes were amplified by reverse transcription-polymerase chain reaction (RT-PCR) and cloned into the pCR2.1 vector (Invitrogen, Carlsbad, Calif.) following previously published protocols (24). The primer pair used for VP2 cloning was WBABglF (5'-GAGATCTATGAACACAA-CAAAGGCAACCGC-3'; SEQ ID NO: 1), containing a 5' Bg/II site, and WBAVP2R (5'-AAGCTTAAGCCCATGT-GTCCATGAC-3'; SEQ ID NO: 2), containing a 5' HindIII site. The primer pair used to clone the VP3 gene was WBAVP3F (5'-GGATCCATGTCAGGGATGGACGAA-GAACTG-3; SEQ ID NO: 3) and FA3'NCHindR (5'-ATAAGCTTGGGGGCCCCCTGGGGGGCC-3'; SEQ ID NO: 4) with BamBI or HindIII sites at the 5' ends respectively. The integrity of the clones was verified by sequencing the plasmid DNA in both directions using an automated DNA sequencer (Applied Biosystems).

To make a yeast expression vector containing the VP2 gene, the VP2-containing plasmid was double digested with Bg/II and HindIII. The VP2 fragment was gel purified, blunt-ended with Klenow enzyme, and inserted between the unique EcoRI and Bg/II sites of pESC-ura, which had been blunt-ended with Klenow, behind the GAL10 promoter (FIG. 1A). To make the VP3 yeast vector, the VP3-containing plasmid was double digested with BamHI and HindIII enzymes. The VP3 fragment was gel purified and cloned between the unique BamHI and HindIII sites of pESC-ura behind the GAL1 promoter (FIG. 1B). Finally, to make the yeast vector that expressed both the VP2 and VP3 capsid protein genes, the VP2 gene was inserted into the unique EcoRI and Bg/II sites of pESC-ura behind the GAL10 promoter in the VP3-containing constructs (FIG. 1C).

Expression of VP2 in Yeast

Yeast (*Saccharomyces cerivisiae* strain YH501; Stratagene, La Jolla, Calif.) were transformed using the EZ Yeast Transformation Kit (Zymed, Sari Francisco, Calif.): Mutant colonies were selected for growth on autotrophic SG-ura medium containing galactose, yeast extract without amino acids, and amino acid dropout mixture (all amino acids plus adenine, no uracil). Mutants were grown at 30° C. for 4 days, collected by centrifugation, then crude protein extracts prepared using Y-PER yeast breaking buffer (Pierce Biotechnology, Rockford, Ill.). Lysates were electrophoresed on 12% SDS-polyacrylamide gels (BioRad, Richmond, Calif.) and transferred to nitrocellulose by electroblotting. The blots were probed with sheep-anti-IPNV polyclonal antibody (Microtek International, Inc, Saanichton, B.C., Canada) and detected with rabbit-anti-sheep polyclonal antibody conjugated to HRP (Bethyl Laboratories, Montgomery, Tex.). Detection was obtained using the colorimetric substrate tetramethyl benzidine (TMB) in a one step solution as described by the manufacturer (Pierce, Rockford, Ill.).

Isolation of rVP2-SVPs and Transmission Electron Microscopy

SVPs were isolated from yeast cultures expressing recombinant VP2 according to a modified protoplasting protocol (18) to remove the yeast cell wall. The cells were lysed by three freeze thaw cycles then sonicated for five 60-second cycles with 20-second intervals. Lipids were removed by performing two successive Freon extractions. SVPs were then purified by passing them through a 26% sucrose cushion at 82,705×g (average) for 4 hours at 4° C. in a swinging bucket rotor (Beckman SW28), followed by CsCl-gradient centrifugation overnight at 115,584×g (average) at 4° C. in a swinging bucket rotor (Beckman SW41). The buoyant density of IPNV is 1.33 grams per cubic centimeter. Bands were withdrawn with a syringe and dialyzed overnight at 4° C. in TN buffer (50 millimolar Tris and 100 millimolar NaCl, pH 8.0) to remove CsCl. SVP's were prepared for negative staining transmission electron microscopy according to the previously published protocols (8). This method of producing SVPs is exemplary; other methods can be used to produce SVPs.

Immunization and Sampling of Rainbow Trout

Rainbow trout (*Oncorhynchus mykiss*; approximately 25 grams) originating from the Clear Springs Food, Inc. (Buhl, Id.) and known to be free of IPNV were used for the immunization experiment. The vaccination and animal work was done at Clear Springs Foods, Inc. while the analytical work was performed at Advanced BioNutrition, Inc. The fish were anesthetized and injected intraperitoneally (EP) with 100 microliters of vaccine (50 microliters of purified rVP2-SVPs containing 100 micrograms antigen and 50 microliters of Freund's Complete Adjuvant). There were three groups of fish: naive fish (n=9), fish injected with adjuvants only (sham-injected treatment; Freund's Complete Adjuvant, Sigma, St. Louis, Mo.; n=8), and a treatment group that was injected with IPNV rVP2-SVPs plus Freud's adjuvant (n=12). Vaccinations were done at days 1 and 32.

For oral vaccination, recombinant yeast expressing rVP2-SVPs (without prior purification) was mixed with feed. Yeast were ground in liquid nitrogen then incorporated into a fish feed (Clear Spring Foods, Inc., proprietary blend) that was first powdered using a coffee mill then supplemented with 10% wheat gluten as binder. Feed blends were mixed by hand with moisture added as required until a pliable dough was produced. This was then fed through a press to produce ribbons of feed that were chopped to approximately 0.5 cm in length. These were allowed to air dry at room temperature for several hours then spray coated with canola oil and frozen until use. The treatments for the oral vaccination include fish that were fed diet containing yeast expressing rVP2-SVPs (n=13) or diet containing non-recombinant yeast (control, n=10). At day 60, blood was withdrawn from caudal vessels of control and vaccinated fish and allowed to clot overnight at 4 degrees Celsius. Blood samples were centrifuged in a tabletop centrifuge at 12,568×g (average) for 5 minutes, then serum was collected and stored at −75 degrees Celsius until analyzed.

Enzyme-Linked Immunosorbent Assay (ELISA)

Immuno Breakapart microplates (Nunc, Rochester, N.Y.) were coated with purified IPNV rVP2-SVPs at 150 micrograms per milliliter in a 50 millimolar carbonate coating buffer (pH 9.6) at 4° C. for 16 hours. Plates were washed 3 times in TBST (IX Tris Buffered Saline (TBS)+0.05% Tween 20) for 5 minutes each wash. The plates were blocked with Ix TBS containing 3% BSA at room temperature. Test sera were diluted 1:32 and 1:64 then 150 microliters was added per well and the plates were incubated for 1 hour at room temperature. Following incubation with test sera, the microplates were washed again 3 times with TBST for 5 minutes per wash. The secondary antibody (rabbit anti-rainbow trout IgG; Jackson ImmunoResearch Laboratories Inc, West Grove. Pa.) was diluted 1:1000 and added to all wells (150 microliters/well). The plates were incubated for 1 hour at room temperature and then washed 3 times in TBST, 5 minutes each wash. Horseradish peroxidase-conjugated goat anti-rabbit IgG (Biosource, Camarillo, Calif.) was added at a 1:1.000 dilution and detected by addition of the colorimetric substrate tetramethyl benzidine (TMB, Pierce, Rockford, Ill.). The absorbance was read at 450 nanometers using a SPECTRAFLUOR® Plus fluorescent plate reader (Tecan, Salzburg, Austria). Negative controls consisted of wells that were coated as above, but a 3% BSA solution was added instead of the fish serum at the capture step.

IPNV Challenge and Sample Collection

Three days after collecting the blood samples (i.e., at 63 days post-vaccination), IPNV challenge was performed by injecting each fish with approximately 250 microliters of $10^7$ $TCID_{50}$/mL of IPNV (Buhl strain, LaPatra unpublished). Naive fish injected with buffer served as negative control for the IPNV challenge. Ten days post-injection, animals were sacrificed, spleen samples collected in TR1 reagent, then stored at −75 degrees Celsius until RNA isolation was performed.

Isolation of Total RNA and cDNA Synthesis

Total RNA was isolated from spleen tissue of control and IPNV-injected rainbow trout using TRI reagent following the manufacturer's protocols (Molecular Research Center, Cincinnati, Ohio). The RNA samples were treated with DNase I (Ambion, Enc, Austin, Tex.) then the RNA quality assessed by running the samples on a 1% formaldehyde agarose gel (23). The cDNA synthesis was carried out in a 40 microliter reaction volume containing 1 microgram total RNA, Ix RT- PCR buffer. 1 millimolar dNTPs, 0.75 micromolar oligo dT, 4 units of RNase inhibitor, and 5 units of MultiScribe reverse transcriptase (Applied Biosystems, Foster City, Calif.) at 42 degrees Celsius for 1 hour. The cDNA was diluted 1:10 using DNase and RNase free molecular biology grade water and 2 microliters of the diluted cDNA was taken for each reaction.

Determining IPNV Load by SYBR Green Real-Time RT-PCR

The primers for the SYBR Green real-time RT-PCR were designed based on the nucleotide sequence of segment A of the IPNV genome that encodes the protease protein (VP4) (GenBank Accession no. NC_001915, forward primer 1916F: 5' AGGAGATGAC ATGTGCTACACCG 3'; SEQ ID NO: 5, and reverse primer 1999R: 5'CCAGCGAATA TTTTCTCCACCA 3'; SEQ ID NO: 6). The rainbow trout elongation factor 1-α (EF-1-α) gene was used as an internal control for normalizing the viral load from sample to sample. The primers for rainbow trout elongation factor 1-α (EF-1-α) were based on the published sequence of these genes (GenBank Accession no AF498320, forward primer 136F: 5' TGATCTACAAGTGCGGAGGCA 3'; SEQ ID NO: 7, and reverse primer 236R: 5' CAGCACCCAGGCATACTTGAA 3'; SEQ ID NO: 8). The primers were designed using the Primer Express Software version 1.0 (Perkin Elmer-Applied Biosystem). The real-time RT-PCR amplifications were performed in a BioRad iCycler iQ (BioRad Laboratories, Inc., Richmond, Calif.).

The SYBR Green real-time RT-PCR mixture contained 12.5 microliters of 2× SYBR. Green Supermix (iQ SYBR Green Supermix), 300 nanomolar each of forward and reverse primers and 2 microliters of the 1:10 diluted cDNA in a 25 microliters reaction volume. The amplifications were carried out in a 96-well microplate with 3 replicates per sample. The thermal profile for SYBR Green real-time RT-PCR was 95 degrees Celsius for 10 minutes, followed by 40 cycles of 95 degrees Celsius for 10 seconds and 60 degrees Celsius for 1 minute.

After a SYBR Green PCR run, data acquisition and subsequent data analyses were performed using the iCycler iQ Real-Time PCR Detection System (BioRad iQ Software Version 1.3). The relative IPNV load in a sample was determined by subtracting the mean $C_t$ values for EF-1α from the mean $C_t$ values of the IPNV amplicon. The differences in the $C_t$ value of the viral genes and the corresponding internal controls were expressed as $\Delta C_t$. The ΔC values were plotted using GraphPad Version 4 (Graphpad Software, Inc., San Diego, Calif.). The difference in the $\Delta C_t$ for one vaccine group compared to the $\Delta C_t$ of the corresponding control was expressed as a $\Delta\Delta C_t$ and 2 represents the difference in viral load between the two treatments.

Results and Discussion

The IPNV segment A has previously been cloned and expressed in hamster fibroblast cells, BHK-21, under the Semliki forest virus promoter and in insect cells under the polyhedrin promoter (polh) and were shown to produce virus-like particles (VLPs) that contain both VP2 and VP3 and are of similar size to the native virus but lack associated nucleic acid (15), (24). However, when we cloned the IPNV segment A in yeast, the polyprotein was expressed but no particles were observed under TEM (data not shown). This might be due to the lack of post-translational processing of the polypeptide in yeast. Therefore, we coexpressed VP2 and VP3 genes under different promoters into the pESC-ura vector so that the post-translational processing of the polyprotein would not be required. For clarity in the following discussion, the authors use the term virus-like particle (VLP) to describe viral-derived particles of similar size to the native virus that lack nucleic acid. For particles that are viral-derived and lack nucleic acid but do not have the same size or shape as the native virus the authors use the term sub-viral particle (SVP) to differentiate the two sets of viral-derived particles.

Cloning of VP2 and VP3 Genes

Figure 2A:
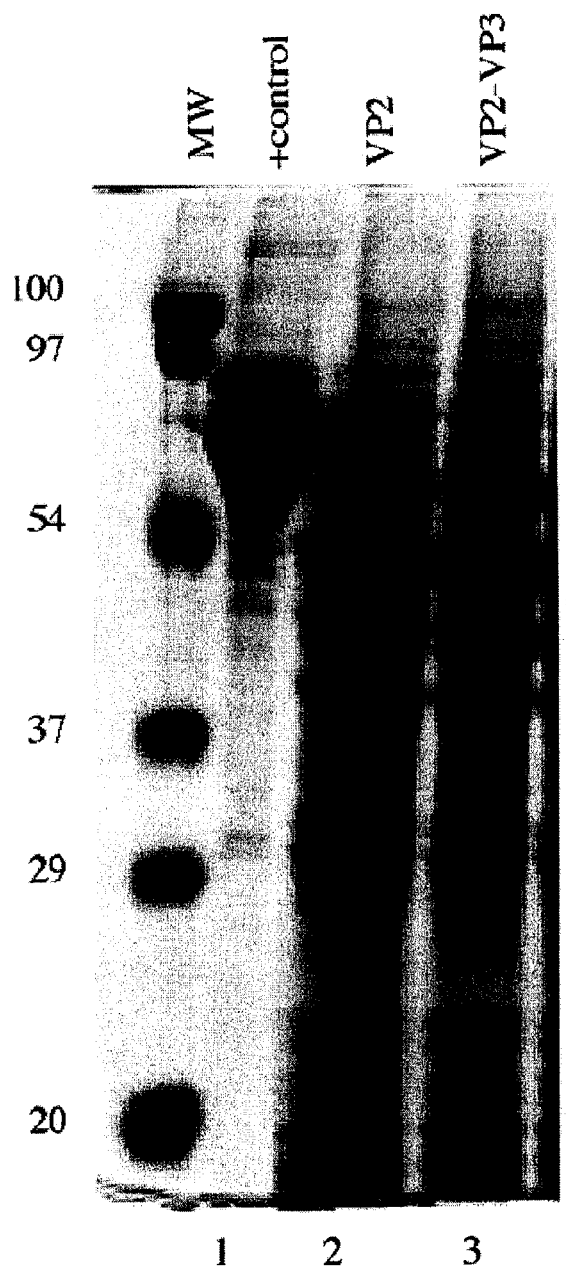
FIG. 2A is an image of a Coomassie blue stained gel of IPNV infected CHSE cell culture supernatant (+ control, lane 1), and Y-PER extracted total yeast protein from the two clones expressing VP2 and VP2+VP3 (lanes 2 and 3).
Figure 2B:
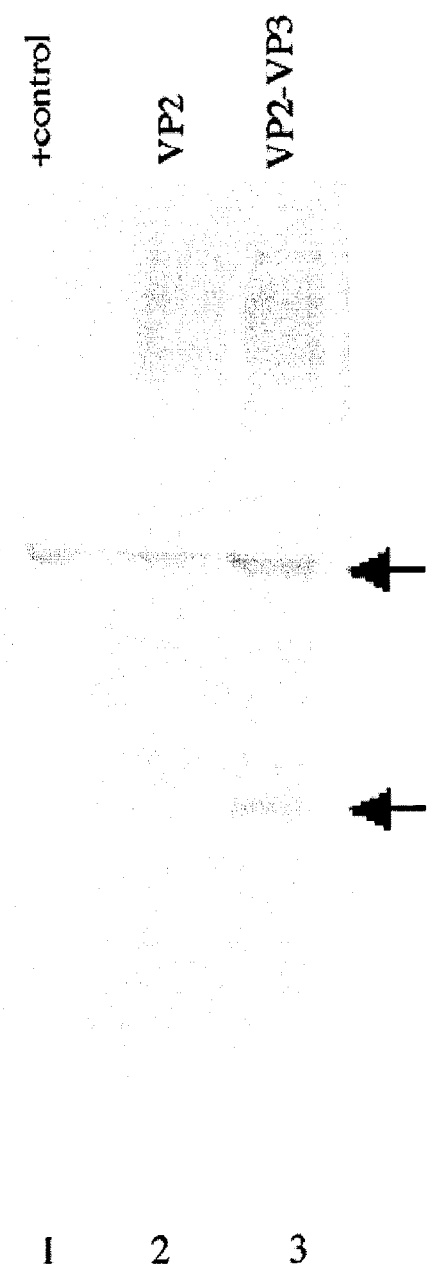
FIG. 2B is an image of an immunoblot of the same samples probed with IPNV polyclonal antibody. The molecular weights of VP2 and VP3 are 54 kDa, and 31 kDa shown by the two arrows. The VP3 band in the positive control (lane 1) was detected at a very low level and is therefore not visible in the scanned photograph.

The predicted mature VP2 and VP3 genes were cloned separately behind GAL10 and GAL1 promoters in pESC-ura. Recombinant yeast containing VP2 or both VP2 and VP3 genes were grown under galactose induction then analyzed by western blot analysis to determine if VP2 and VP3 were expressed (FIG. 2). Two bands were observed that corresponded roughly to the molecular weights predicted for VP2 and VP3 in the co-expression system, 54 kDa and 31 kDa respectively (FIG. 2, right panel). The immune blots indicated the presence of both VP2 and VP3 in our yeast mutant designed to express both genes when grown under galactose induction.

Preparation of SVPs and/or VLPs Plus Subsequent Electron Microscopy

Figure 3:
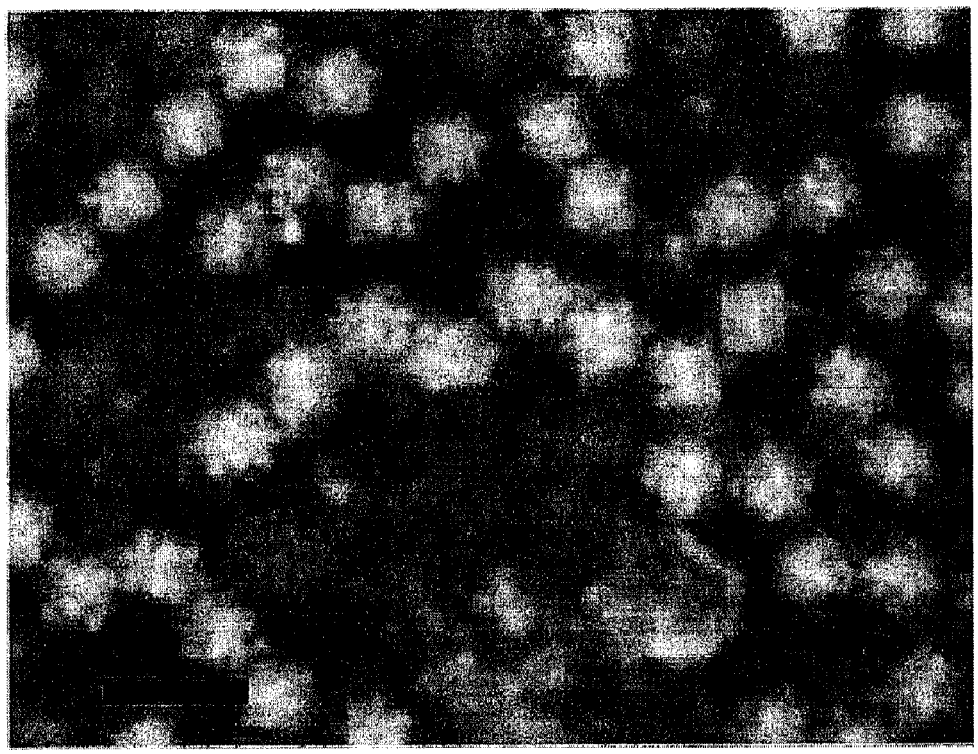
FIG. 3 is a transmission electron micrograph of cesium chloride gradient purified rVP2-SVPs negatively stained with sodium phosphotungstate. The marker bar indicates a distance of 40 micrometers.

Using the methods described above, VLP or SVP preparations were prepared on the clones containing both VP2 & VP3 genes. Several areas of high density were observed in the CsCl gradients. The high molecular weight materials pelleted in the ultracentrifuge, and a band of moderate density was observed in the gradient. The moderate density band corresponded to a approximately 20 nm particle that contained only VP2 reacting materials (FIG. 3). However, 60 nm full sized IPNV virus-like particles, as seen previously in IPNV segment A expression in insect cells (24), were not observed. Similar particles have been previously described for IPNV (10) and are thought to be due to an error in pVP2 processing. Similar particles were also observed and characterized in IBDV (20). They are formed by 20 VP2 subunit trimers in a T=1 fashion. VP3 is not involved in their formation. Here, we saw the same thing whether VP2 was expressed in yeast simultaneously with the VP3 gene or alone in yeast. These particles are referred to herein as sub-viral particles (SVPs). Similar methods can be used to produce SVPs for similar viruses (e.g., other viruses having capsid proteins from which SVPs can be formed, such as other Birnaviridae family viruses and other viruses for which salmonids or other fish are a host). The compositions described herein can be produced by a variety of methods available to skilled worker in this field, and SVPs made by any of these methods are expected to be useful in the methods described herein.

Immunization of Rainbow Trout

Figure 4:
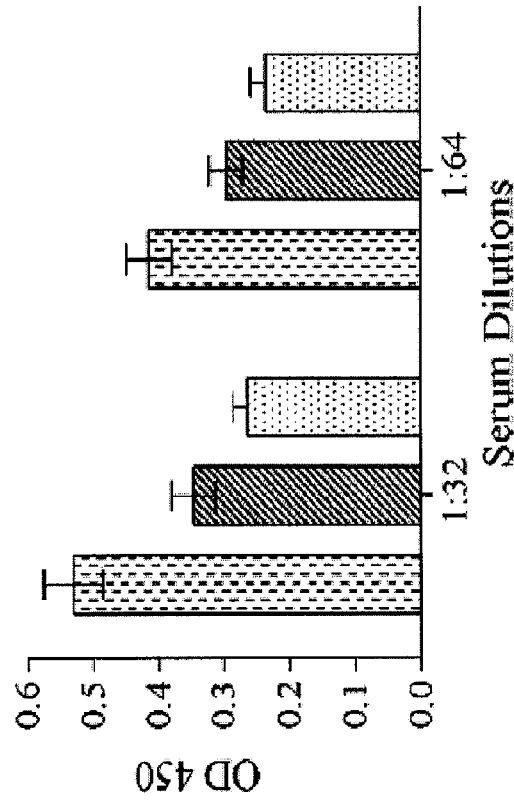
FIG. 4, consisting of FIGS. 4A and 4B, is a pair of bar graphs indicating mean ELISA values (expressed as the absorbance of the HRP substrate TMB at $A_{450}$) of serum from responding fish following immunization with IPNV rVP2-SVPs.
Figure 4:
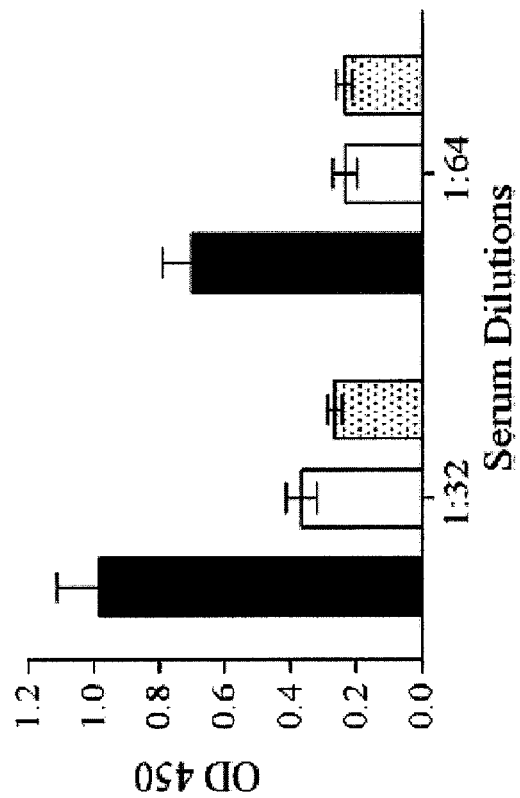

Rainbow trout that were free of IPNV were used for a vaccination experiment testing both intraperitoneal injection (IP) with adjuvant and by oral delivery in feed. The rVP2-SVPs were delivered either as purified SVPs (for IP injection) or as crude yeast lysate incorporated into feeds (for oral delivery) to test the antigenicity of these IPNV subunit vaccines in particle form in rainbow trout. The experimental design is outlined in Table 1. To test the ability of rVP2-SVPs to induce anti-IPNV antibody production, the most direct method is to use purified antigen and deliver by injection. Purified rVP2-SVPs were delivered by IP injection with Freud's adjuvant as described in Tables 1 and 2. A booster of the same composition was delivered after 32 days and fish bled at 63 days. All of the injected fish had significantly higher titers of anti-IPNV antibodies than either the naive or sham-injected controls (FIG. 4A). The naive fish and the sham-injected fish were not significantly different from each other at the 95% confidence interval when compared using the student's t-test. The purified rVP2-SVP injected fish showed 100% seroconversion (Table 2; FIG. 4A). Student's t-tests were run in Statview Version 5.01 (SAS Institute, Inc.), testing for significant differences between antibody titers of vaccine injected or fed animals compared to both the naive fish and sham-injected fish (negative controls). At the 1:32 serum dilution, the rVP2-SVP injected fish had a significantly higher seroconversion rate when compared to the naive fish (p=0.013) and the sham-injected fish (p=0.001). The 1:64 serum dilution also demonstrated significant seroconversion differences between rVP2-SVP injected fish and negative controls (p=0.0003, naive fish and p=0.0007, sham-injected fish).

Oral vaccination would provide a number of advantages over injection such as ease of use, ability to vaccinate smaller fish, lower cost of vaccine, and easy ability to make multivalent vaccines (through delivery of different clones in the feeds). In order to test the ability of rVP2-SVPs to induce an immune response, recombinant yeast expressing VLPs were incorporated into fish feed and fed to one treatment group for seven days. At day 32 another seven day feeding of the recombinant yeast containing feed was done as a booster (Table 1). At 63 days the fish were bled and the anti-IPNV titers compared to that found in naive fish and fish fed a control feed supplemented with wild-type yeast in place of the recombinant yeast (FIG. 4B). It was apparent that the orally vaccinated fish had an immune response greater than that observed in either naive or yeast control fed fish (p=0.0002 for naive fish and p=0.0053 for yeast control). There appeared to be a higher anti-IPNV titer in the yeast control sera than in the naive fish, but the difference was not significant (p=0.1645) as determined by the student t-test. Seroconversion of the orally vaccinated fish was slightly less than that observed in the IP injected animals with approximately 75% conversion (Table 2). Oral vaccination with rVP2-SVPs provides an increase, albeit reduced relative to IP injection, in anti-IPNV titer.

While these data do not demonstrate the effectiveness of these vaccination strategies on prevention of disease, they are an indication that oral vaccination could potentially provide an alternative to IP injection vaccination for the treatment of IPN. A challenge trial would provide definitive evidence that this approach could prevent disease.

The results presented herein pertain to rainbow trout. However, the methods and compositions are not so limited in their applicability. One expects such compositions and methods to be effective in other types of fish as well, including not only salmonids. Furthermore, the efficacy of the compositions described herein for enhancing immunity and preventing disease are not limited to the methods of administration that are explicitly described herein. Other methods of administering immunogenic compositions to fish are expected to yield similar efficacy.

IPNV Challenge/Viral Load

Figure 5B:
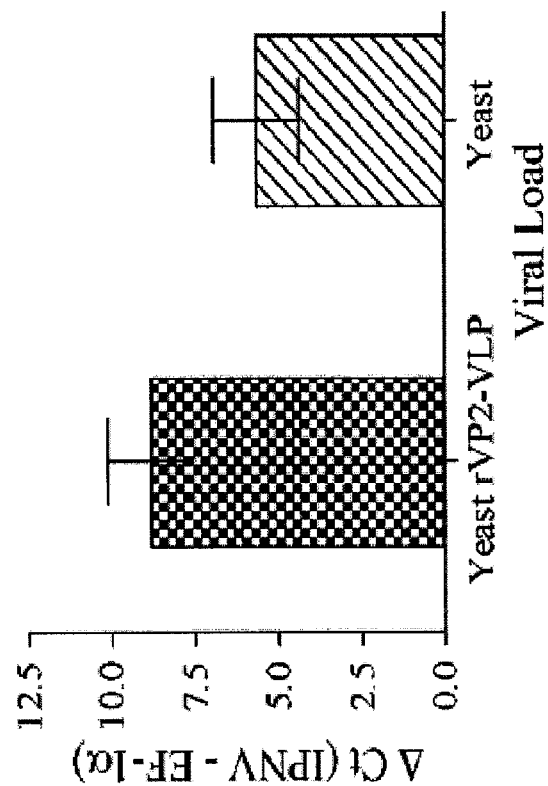
FIG. 5B shows represents the IPNV load in rainbow trout that were orally vaccinated (diet containing yeast expressing rVP2-SVPs) (checkered bar, n=12), or control fish (diet containing yeast only) (striped bar, n=11). The IPNV load was normalized with respect to rainbow trout EF-1-α expression. The $\Delta C_t$ values are inversely correlated to IPNV copy number. Therefore, lower the $\Delta C_t$ value higher the IPNV load. The error bars represent 1 SEM.
Figure 5A:
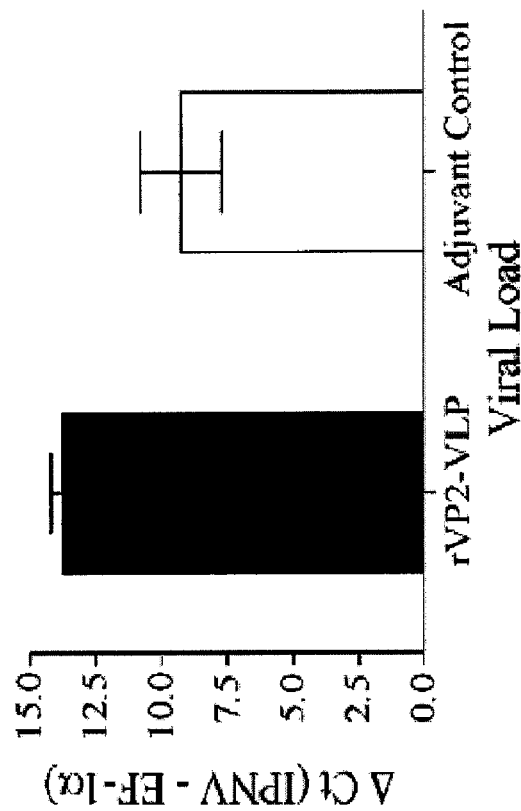
FIG. 5A shows IPNV load in rVP2-SVP injected (filled bar, n=12), and adjuvant injected (open bar, n=8) rainbow trout.

There is no good challenge system for IPNV with mortality as the endpoint (1). Using IPNV viral load, as determined by real-time RT PCR, could provide a convenient method to track the progress of the disease. In this study, the trout were vaccinated with either rVP2-SVPs delivered in feed or by injection of purified rVP2-SVPs derived from the West Buxton strain of IPNV. After 63 days post-vaccination, fish were injected with the Buhl strain of IPNV that had been isolated from rainbow trout in Idaho (La Patra, unpublished data). This was a different IPNV strain (Buhl) than that from which the rVP2-SVPs vaccine was derived (West Buxton strain). Therefore, the challenge was with a heterologous strain and may help evaluate the specificity of this approach. IP vaccinated rainbow trout had significantly less virus (p=0.0280) (22 fold) than sham-injected control fish (Table 3, FIG. 5). When oral vaccinates were compared to the yeast only controls, a 12-fold reduction in virus was found for IPNV vaccinated fish (FIG. 5B). This difference was visually apparent, but not significant at the 0.05 level (p=0.1179).

These data indicate that rVP2-SVPs produced in yeast could provide a novel means for amplification of a protective immune response in rainbow trout, and by extension to salmonid species like salmon, either by injection or by delivery in feeds. Expression of a rVP2-SVP particle in yeast provides an interesting opportunity for its use as a vaccine for trout and salmon. The ability of these particles to induce the production of IPNV-specific antibodies was demonstrated by both oral and injection routes. The potential for use of the oral route as a vaccine needs further investigation to optimize the immune response and determine if the observed decrease in viral load directly correlates with prevention of IPN. This study sets the foundation for further studies to test in juvenile salmonids the utility of this approach to prevent early onset of IPN.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

REFERENCES

Literature referred to herein is as follows:
(1) Biering, E., S. Villoing, I. Sommerset, K. E. Christie. 2005. Update on viral vaccines for fish In: P. J. Midtlyng (ed.), Progress in Fish Vaccinology. Dev. Biol. Basel 121: 97-113.
(2) Botteher, B., N. A. Kiselev, V. Y. Stel'Mashchuk, N. A. Perevozchikova, A. V. Borisov, and R. A. Crowther. 1997. Three-dimensional structure of infectious bursal disease virus determined by electron cryomicroscoopy. J Virol 71(1): 325-330.
(3) Brun, E. 2003. Epidemiology. In: O. Evensen, E. Rimstad, R. Stagg, E. Brun, P. Midtlyng, B. Skjelstad. L. H. Johansen, and I. Jensen (eds.), IPN in salmonids: a review. FHL & VESO, Trondheim, Norway, pp. 51-67.
(4) Christie, K. E. 1997. Immunization with viral antigens: infectious pancreatic necrosis. Dev. Biol. Stand. 90: 191-199.
(5) Delmas, B., Kibenge, F. S. B., Leong, J. A., Mundt, E., Vakharia, V. N., Wu, J. L., 2005. Birnaviridae, p. 561-569. In C. M. Fauquet, M. A. Mayo, J. Maniloff, U. Desselberger, and A. L. Ball (ed.), Virus Taxonomy. Academic Press, London, U.K.
(6) Dobos, P., 1995. The molecular biology of infectious pancreatic necrosis virus (IPNV). Ann. Rev. Fish Dis. 5, 24-54.
(7) Duncan, R., Mason, C. L, Nagy, E., Leong, J. A., Dobos, P., 1991. Sequence analysis of infectious pancreatic necrosis virus genome segment B and its encoded VP1 protein: a putative RNA-dependent RNA polymerase lacking the Gly-Asp-Asp motif. Virology 181(2), 541-552.
(8) Dykstra M J. (1.992) Specimen preparation for transmission electron microscopy. In Dykstra M J. ed. Biological Electron Microscopy. New York, London, Plenum Press, 5-78.
(9) Frost P., L. S. Havarstein, B. Lygren, S. Stahl, C. Endresen, K. E. Christie. 1995. Napping of neutralization epitopes on infectious pancreatic necrosis viruses. J. Gen. Virol. 76 (Pt 5): 1165-1172.
(10) Galloux, M., C. Chevalier, C. Henry, J.-C. Huet, B. Da Costa, B. Delmas 2004. Peptides resulting from the pVP2 C-terminal processing are present in infectious pancreatic necrosis virus particles. J. Gen. Virol. 85(Pt 8): 2231-2236.
(11) Gorbalenya. A. E., F. M. Pringle, J. L. Zeddam, B. T. Luke, C. E. Cameron, J. Kalmakoff, T. N. Hanzlik, K. H. Gordon, and V. K. Ward. 2002. The palm subdomain-based active site is internally permuted in viral RNA-dependent RNA polymerases of an ancient lineage. J. Mol. Biol. 324 (1): 47-62.
(12) Heppell J., E. Tarrab, J. Lecomte, Berthiaume, and M. Arella. 1995. Strain variability and localization of important epitopes on the major structural protein (VP2) of infectious pancreatic necrosis virus. Virology 214 (1): 40-49.
(13) Labus, M. B., S. Breeman, A. E. Ellis, D. A. Smail, M. Kervick and W. T. Melvin. 2001. Antigenic comparison of a truncated form of VP2 of infectious pancreatic necrosis (IPN) virus expressed in four different cell types. Fish & Shellfish Immunology 11(3): 203-216.
(14) Magyar, G. and P. Dobos. 1994. Evidence to the detection of the infectious pancreatic necrosis virus polyprotein and the 17 kDa polypeptide in infected cells and the NS protease in purified virus. Virology 204(2): 580-589.
(15) McKenna, B. M., R. M. Fitzpatrick, K. V. Phenix, D. Todd, L. M. Vaughan and G. J. Atkins. 2001. Formation of infectious pancreatic necrosis virus-like particles following expression of segment A by recombinant semliki forest virus. Marine Biotechnology 3(2): 103-110.
(16) Melby, H. P., Caswell-Reno, and K. Falk. 1994. Antigenic analysis of Norwegian aquatic birnavirus isolates uwin monoclonal antibodies J. Fish Dis. 17: 85-91.
(17) Midtlyng, P. 2003. Vaccination. In: Evensen O, Rimstad E, Stagg R, Brun E, Midtlyng P., Skjelstad B. Johansen L H, Jensen I (eds.), IPN in salmonids: a review. FHL & VESO, Trondheim, Norway, pp. 85-95.
(18) Pannunzio, V. G., Burgos, H. I., Alonso, M., Ramos, E. H., Mattoon, J. R., Stella, C A. 2004. Yeast Plasmids with the Least Trouble. Promega Notes #87: 27-28.
(19) Pitcovski, J., B. Gutter, et al. (2003). "Development and large-scale use of recombinant VP2 vaccine for the prevention of infectious bursal disease of chickens." Vaccine 21(32): 4736-43.
(20) Pous, J., C. Chevalier, M. Ouldali, J. Navaza, B. Delmas and J. Lepault. 2005. Structure of birnavirus-like particles determined by combined electron cryomicroscopy and X-ray crystallography. J. Gen. Virol. 86(Pt 8): 2339-2346.
(21) Roberts, R. J. and M. D. Pearson 2005. Infectious pancreatic necrosis in Atlantic salmon, Salmo salar L. J. Fish Diseases 28(7): 383-390.
(22) Romanos, M. A., C. A. Scoer, and J. J. Clare. 1992. Foreign gene expression in yeast: a review. Yeast 8(6): 423-488.
(23) Sambrook, J., E. F. Fritsch and T. Maniatis. 1989. Molecular cloning: a laboratory manual, 2nd ed. Cold Spring Harbor Laboratory, Cold Spring Harbor, N.Y.
(24) Shivappa, R. B., P. E. McAllister, G. H. Edwards, N. Santi, O. Evensen, and V. N. Vakharia. 2005. Development of a subunit vaccine for infectious pancreatic necrosis virus using a baculovirus insect/larvae system. In: P. J. Midtlyng (ed.) Progress in Fish Vaccinology. Dev. Biol. Basel 121: 165-174.
(25) WolfK., S. Snieszko, C. Dunbar, E. Pyle. 1960. Virus nature of infectious pancreatic necrosis in trout. Proc. Soc. Exp. Biol. Med. 104: 105-108.
(26) Yao, K. and V. N. Vakharia. 1998. Generation of infectious pancreatic necrosis virus from cloned cDNA. J. Virol. 72(11): 8913-8920.

TABLE 1

Experimental design for vaccination trial on rainbow trout with IPNV rVP2-SVPs delivered by either intraperitoneal injection (IP) or orally in feeds.

| Treatment | Vaccine delivery (Injection/feeding)* Initial (Day) | Booster (Day) | No. of Animals/ Treatment |
|---|---|---|---|
| Naïve fish | None (Day 1) | None (Day 32) | 9 |
| Injection Control | Injection (Day 1) | Injection (Day 32) | 8 |
| Injected rVP2-SVPs | Injection (Day 1) | Injection (Day 32) | 12 |
| Control Yeast | Oral (Days 1-7) | Oral (Days 32-38) | 10 |
| Oral rVP2-SVPs Yeast | Oral (Day 1-7) | Oral (Days 32-38) | 13 |

TABLE 2

Effect of intraperitoneal or oral vaccination with IPNV rVP2-SVPs on the titer of anti-IPNV antibodies in rainbow trout.

| Treatments* | Vaccine delivery | Serum Dilution | Mean $A_{450}$ value ± SEM | Seropositives/ Total Number** |
|---|---|---|---|---|
| Naïve fish | None | 1:32 | 0.263 ± 0.022 | 0 |
| | | 1:64 | 0.235 ± 0.023 | 0 |
| Adjuvant Control | Injection | 1:32 | 0.363 ± 0.049 | 0 |
| | | 1:64 | 0.232 ± 0.037 | 0 |
| rVP2-SVPs | Injection | 1:32 | 0.982 ± 0.128 | 12 of 12 |
| | | 1:64 | 0.701 ± 0.090 | 12 of 12 |
| Control yeast | Oral | 1:32 | 0.346 ± 0.035 | 0 |
| | | 1:64 | 0.295 ± 0.026 | 0 |
| rVP2-SVPs Yeast | Oral | 1:32 | 0.530 ± 0.045 | 10 of 13 |
| | | 1:64 | 0.414 ± 0.034 | 9 of 13 |

*Naive fish were not injected and were fed normal fish feed, adjuvant control fish were IP injected with buffer and adjuvant, rVP2-SVPs fish were injected with 100 μg of antigen plus adjuvant. control yeast fish were fed fish feed supplemented with wild-type yeast, and rVP2-SVPs yeast fish were fed fish feeds containing the recombinant yeast.
**Fish considered seropositive if $A_{450}$ was above the mean adjuvant control plus one standard error.

TABLE 3

Relative quantification of IPNV load by real-time RT-PCR in rVP2-SVP vaccinated rainbow trout.

| Treatments | Vaccine Delivery Injection/Feeding | | Average ΔCt* | ΔΔ Ct** | IPNV Fold reduction ($2^{\Delta\Delta Ct}$) |
|---|---|---|---|---|---|
| Adjuvant control | Injection (Day 1) | Injection (Day 32) | 9.27 | | |
| rVP2-SVPs | Injection (Day 1) | Injection (Day 32) | 13.75 | 4.49 | 22.40 |
| Control Yeast | Oral (Days 1-7) | Oral (Days 32-38) | 5.22 | | |
| rVP2-SVPs Yeast | Oral (Days 1-7) | Oral (Days 32-38) | 8.83 | 3.61 | 12.25 |

*ΔCt was first calculated for each fish using the Ct values of IPNV for a fish minus the Ct values of EF-I alpha gene for the same fish. Then the average ΔCt was calculated taking the Ct value of all the fish in each treatment.
**ΔΔ Ct = Average ΔCt value of a treatment minus the average ΔCt value of the corresponding control treatment

What is claimed is:

1. A composition comprising aquatic species feed and a crude yeast lysate, wherein the crude yeast lysate comprises a recombinant yeast expressing Infectious Necrosis Virus segment A protein consisting of capsid protein 2 (VP2) as recombinant VP2 sub-viral particles (rVP2-SVPs), wherein the rVP2-SVPs are not purified from the yeast and wherein the rVP2-SVPs are about 20 nanometers in diameter size.

2. The composition according to claim 1, wherein the aquatic species feed is fish food for oral administration to fish for controlling Infectious Pancreatic Necrosis Virus (IPNV) therein.

3. The composition according to claim 1, wherein the yeast does not generate pyrogens that must be removed before administration to an aquatic species.

4. An oral vaccine for controlling Infectious Pancreatic Necrosis Virus (IPNV), wherein the oral vaccine comprises the recombinant yeast according to claim 1.

5. The oral vaccine according to claim 4, wherein the recombinant yeast was mixed with aquatic feed for feeding to an aquatic species.

6. A method to enhance immunity against IPNV comprising:

administering an effective amount of the composition according to claim 1 to aquatic species for a period of at least seven days.

7. A method of generating a composition comprising aquatic species feed and a crude yeast lysate comprising the steps of:
  (a) providing a recombinant yeast expression vector comprising a polynucleotide encoding IPNV Segment A proteins consisting of capsid protein 2, VP2;
  (b) transfecting yeast with the recombinant yeast expression vector; and
  (c) maintaining suitable conditions for expression of rVP2-sub-viral particles (SVPs) of Infectious Pancreatic Necrosis Virus (IPNV);
  (d) harvesting the yeast that expressed rVP2-SVPs; and
  (e) combining the yeast that expressed rVP2-SVPs with the aquatic species feed, wherein the rVP2-SVPs are not purified or isolated from the yeast and wherein the rVP2-SVPs are about 20 nanometers in diameter size.

8. The method according to claim 7, wherein the aquatic species feed is fish food for oral administration to fish for controlling IPNV therein.

* * * * *